United States Patent
Wang et al.

(10) Patent No.: US 8,230,748 B2
(45) Date of Patent: Jul. 31, 2012

(54) APPARATUS FOR PRE-STRESS-STRAINING ROD-TYPE SPECIMENS IN TENSION FOR IN-SITU PASSIVE FRACTURE TESTING

(75) Inventors: John Jy-an Wang, Oak Ridge, TN (US); Ken C. Liu, Oak Ridge, TN (US); Zhili Feng, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 323 days.

(21) Appl. No.: 12/498,877

(22) Filed: Jul. 7, 2009

(65) Prior Publication Data
US 2011/0005332 A1 Jan. 13, 2011

(51) Int. Cl.
*G01N 3/02* (2006.01)
(52) U.S. Cl. .......................................... 73/856
(58) Field of Classification Search .............. 73/856
See application file for complete search history.

(56) References Cited

U.S. PATENT DOCUMENTS

| | | | | |
|---|---|---|---|---|
| 3,572,102 A | * | 3/1971 | Baratta ............................ | 73/856 |
| 4,198,870 A | * | 4/1980 | Barker et al. .................... | 73/799 |
| 4,235,114 A | * | 11/1980 | Mohler ............................ | 73/805 |
| 5,265,461 A | * | 11/1993 | Steiger et al. .................... | 73/38 |
| 5,388,464 A | * | 2/1995 | Maddison ........................ | 73/856 |
| 5,425,276 A | * | 6/1995 | Gram et al. ...................... | 73/816 |
| 5,798,463 A | * | 8/1998 | Doudican et al. ................ | 73/789 |
| 5,945,607 A | * | 8/1999 | Peppel et al. .................... | 73/856 |
| 6,023,980 A | * | 2/2000 | Owen et al. ...................... | 73/797 |
| 6,647,802 B2 | * | 11/2003 | Willson-Hackworth et al. ................................ | 73/826 |
| 6,813,960 B1 | * | 11/2004 | Owen et al. ...................... | 73/808 |

* cited by examiner

*Primary Examiner* — Lisa Caputo
*Assistant Examiner* — Octavia Davis-Hollington
(74) *Attorney, Agent, or Firm* — Luedeka Neely Group, P.C.

(57) ABSTRACT

A stress-strain testing apparatus imposes a stress-strain on a specimen while disposed in a controlled environment. Each end of the specimen is fastened to an end cap and a strain gage is attached to the specimen. An adjusting mechanism and a compression element are disposed between the end caps forming a frame for applying forces to the end caps and thereby stress-straining the specimen. The adjusting mechanism may be extended or retracted to increase or decrease the imposed stress-strain on the specimen, and the stress-strain is measured by the strain gage on the specimen while the apparatus is exposed to an environment such as high pressure hydrogen. Strain gages may be placed on the frame to measure stress-strains in the frame that may be caused by the environment.

24 Claims, 12 Drawing Sheets

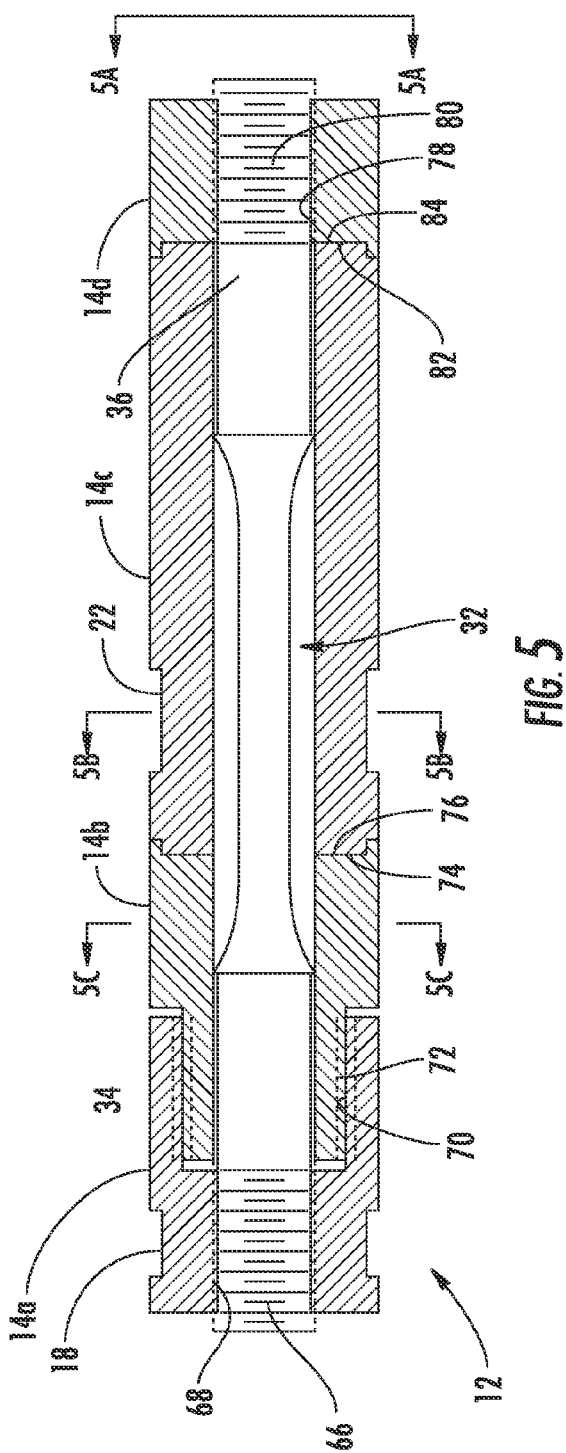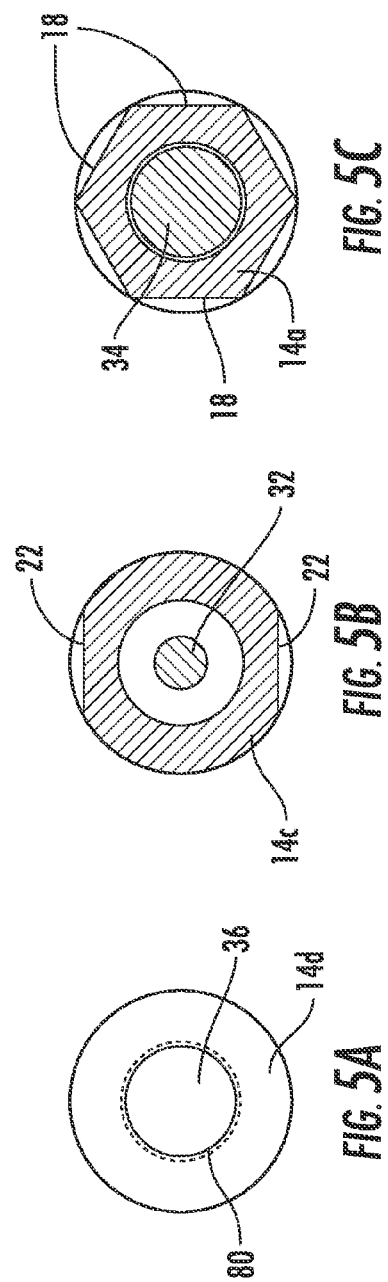

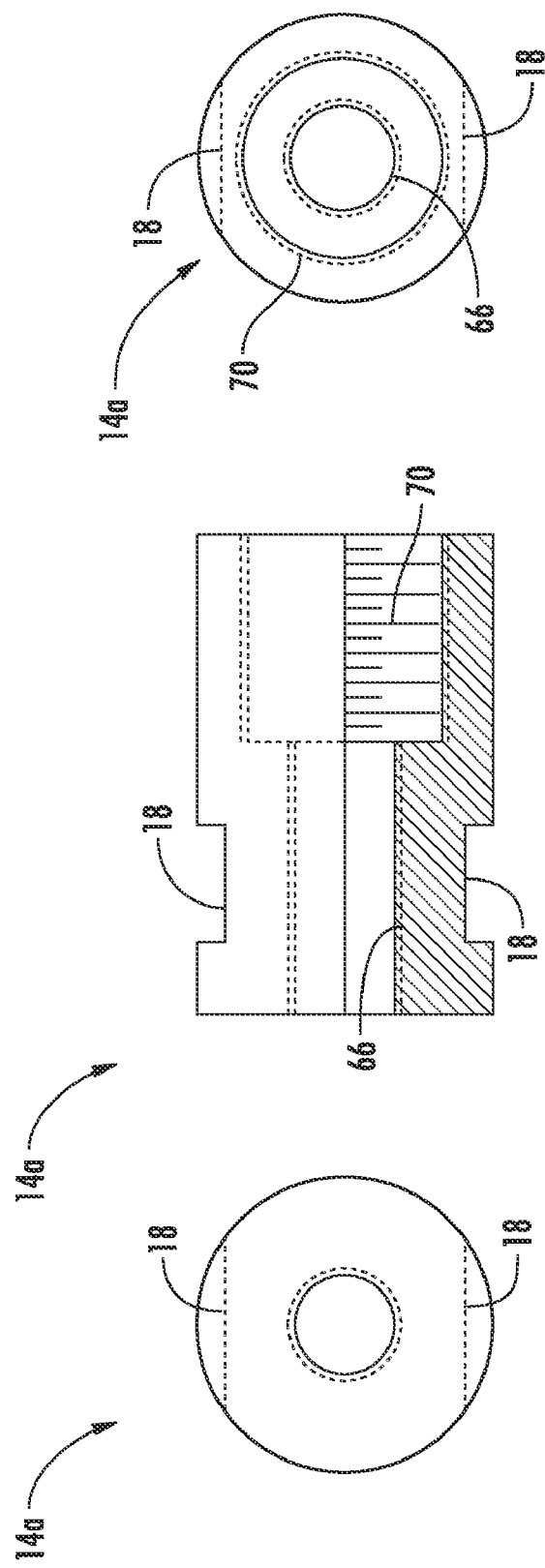

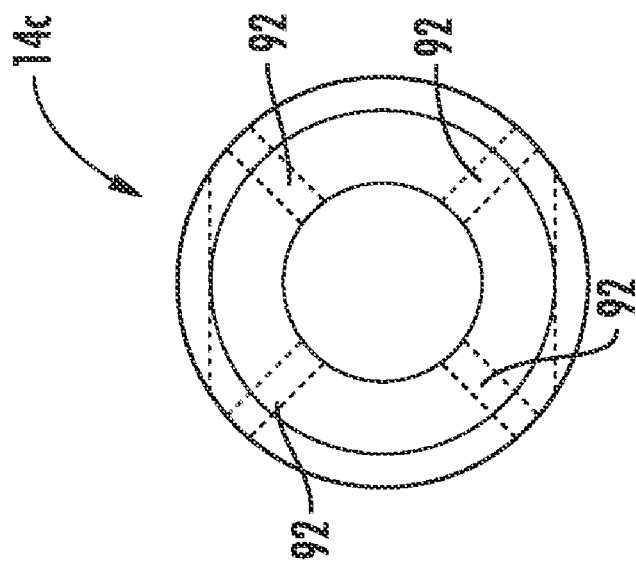
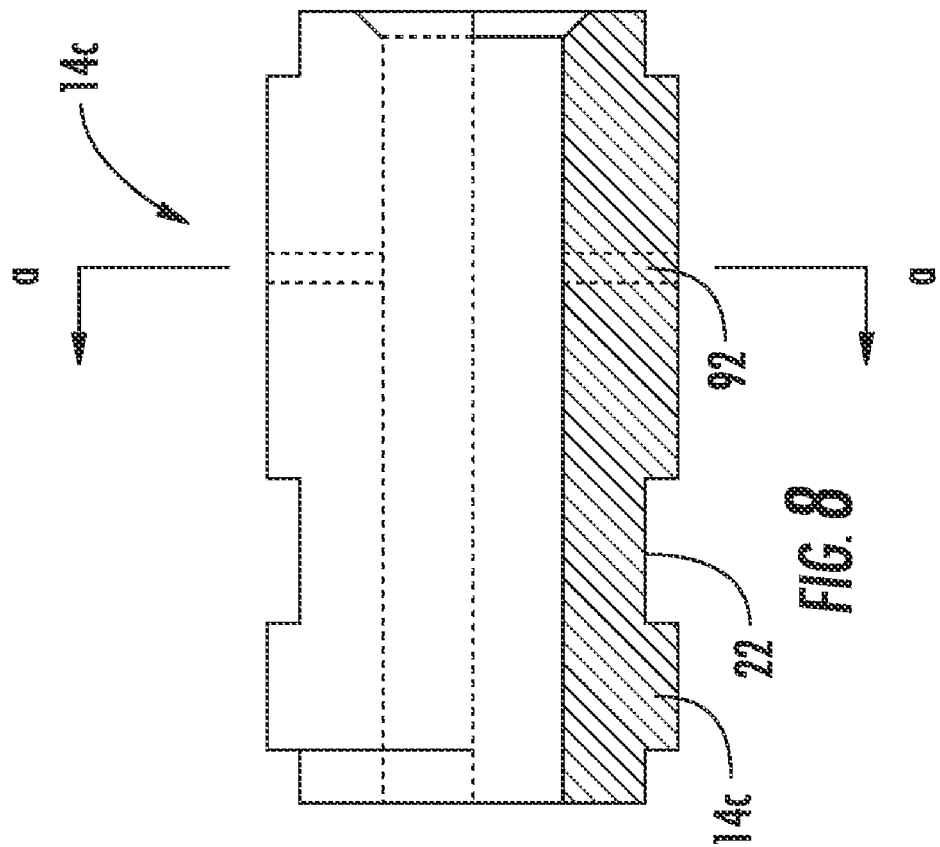

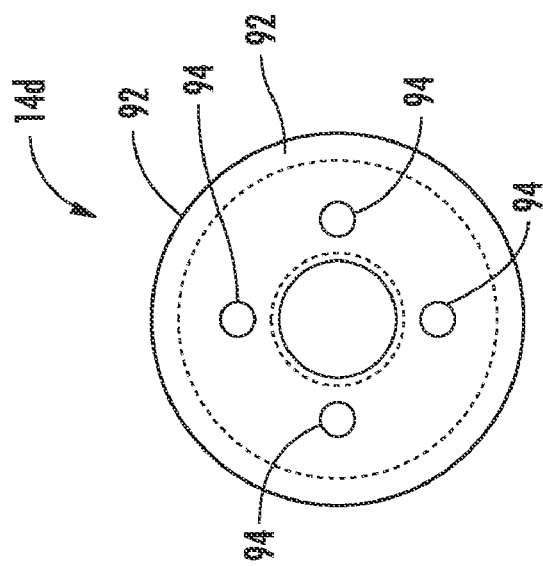
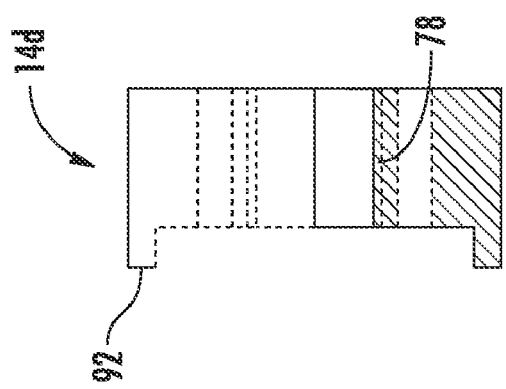
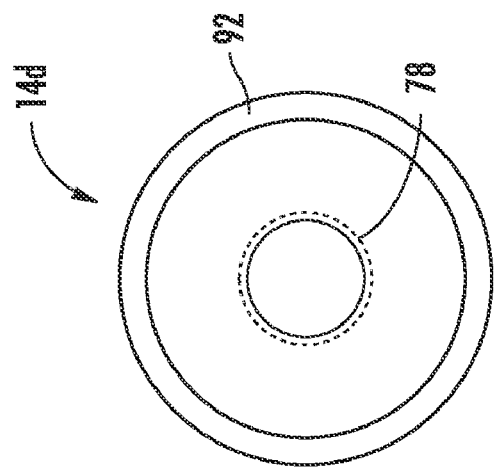

APPARATUS FOR PRE-STRESS-STRAINING ROD-TYPE SPECIMENS IN TENSION FOR IN-SITU PASSIVE FRACTURE TESTING

GOVERNMENT RIGHTS

This invention was made with government support under Contract No. DE-AC05-00OR22725 awarded by the U.S. Department of Energy. The government has certain rights in the invention.

FIELD

The present invention relates to the field of material testing and particularly relates to the field of testing material properties in the environmental chambers containing high pressure gases such as hydrogen.

BACKGROUND

Methods to generate fracture toughness values of materials, such as metallic and ceramic materials, have been recommended by the American Society for Testing and Materials (ASTM) and widely accepted as standard test methods by the scientific community. A wealth of test data has been obtained by these methods and reported and evaluated for many types of materials. However, the data shows scatter and inconsistency even within a family of the same material type and the differences appear irreconcilable. Lack of provisions to account for specimen size effects, in homogeneity of materials and other factors can be cited as causes of these inconsistencies.

Inconsistencies in fracture toughness evaluation can be further complicated when evaluating welds which inherently consist of three zones of different phases known as the weld zone, the heat affected zone, and the base material. Each of these zones is likely to manifest a characteristically different microstructure and mechanical properties. The fracture behavior of the fused line that lies between the solidified weld zone and the heat affected zone is not well explored due to the lack of standard test methods for these types of structures.

In addition, influences of gasses or other environmental features on the behavior of a weldment are not well known, but the information is important and needed for energy development programs. In particular, the influence of hydrogen on materials and particularly weld zones is important information that is missing or inconsistent in the current literature. The conventional methods of measuring in-situ crack behavior of weld material are typically not physically suitable or economically viable in extremely high pressure environments of hydrogen.

SUMMARY

Considering the above problems, embodiments are disclosed herein for placing a stress-strain on a specimen for testing the specimen in harsh environments such as a high pressure hydrogen environment. In this discussion the term stress-strain will be used in a broad sense to refer to the status, condition or forces associated with a particular body. In science, strain is the deformation of a body caused by the application of force or stress, and stress is a force per unit as applied to a body that produces strain. Stress is measured in units of force divided by units of area. In the embodiments described herein, strain is often measured and used to determine stress, so that a strain measurement is an indirect stress measurement. Also in a technical sense, a strain gage may be construed as actually measuring a stress experienced by the gage, as opposed to a strain experienced a body to which the gage is attached. So as to describe the embodiments broadly, stress-strain is often used to signify that strain or stress or both are measured (directly or indirectly) or created. The use of "stress-strain" is intended to avoid the possible narrowing of the concepts by speaking only in terms of either stress or strain.

In accordance with one embodiment disclosed herein, a stress-strain testing apparatus includes first and second end caps. A specimen is attached between the first and second end caps and is tested under a condition of stress-strain. A frame is disposed between and engages the first and second end caps, and the frame includes an adjusting mechanism. When an external force is applied to the adjusting mechanism, it extends apart and applies opposed forces on the first and second end caps to thereby impose a tension force and stress-strain on the specimen. A strain gage is disposed to measure stress-strain imposed by the frame on the specimen. The strain gage may be mounted on the frame alone to directly measure stress-strain on the frame and indirectly measure stress-strain on the specimen. Or, the strain gage may be mounted on the specimen alone to directly measure stress-strain on the specimen and indirectly measure stress-strain on the frame. Dummy strain gages may be mounted in places that are not affected by the stress-strain produced by the frame and these strain gages will measure changes in the gages caused by the environment and such changes may be factored out of the calculation of the stress-strain on the frame and specimen.

In one embodiment, the strain gage is applied to the specimen and each specimen may be individually calibrated to determine the stress-strain created by a known force. For example, a series of known tension forces may be applied to the specimen and the output of the strain gage is taken for each force. The actual stress being applied to the specimen at its narrowest diameter is determined for each known force by dividing the known force by the smallest cross-sectional area of the specimen. So, for each known force, there is calculated a known stress and that stress is correlated to the output from the strain gage, thereby creating a lookup table of stresses for various outputs from the strain gage. When the gage is later used to measure the forces on the specimen, the output of the strain gage and the lookup table and interpolation may be used to determine the stress on the specimen when a particular output is produced by the strain gage.

In embodiments where the strain gages are mounted on the frame and not the specimen, a similar calibration is done, except it is not possible to calculate stress on a specimen because the specimen sizes may differ. Thus, the calibration table uses a series of forces, as opposed to stresses, charted against the output of the strain gage that is mounted on the frame. When the specimen or specimens are known, stress may be calculated by dividing each calibration force in the table by smallest cross sectional area of the specimen.

In a particular embodiment, the frame is a compression column having a tubular shape and having an interior dimensioned to receive the specimen and allow it to pass through the compression column and attach to the first and second end caps. In this embodiment, the frame also includes an adjusting cylinder with threads formed in one end. Threads are also formed in the first end cap dimensioned to mate with the threads on the adjusting cylinder. The adjusting cylinder is threaded into the end cap so that the adjusting cylinder may be rotated relative to the end cap to thereby move the adjusting cylinder towards or away from the end cap. In this manner, the adjusting cylinder extends to create the opposing forces that are applied to the first and second end caps through the frame. The adjusting cylinder and the compression column have shoulders that are configured to concentrically engage and transmit compression forces between the adjusting cylinder and the compression column. However, the shoulders are configured to allow rotational sliding motion between the adjusting cylinder and the compression column. Utilizing this structure, the expansion cylinder may be rotated with respect to the first end and with respect to the compression column and apply a compression force to the second end without rotating the first end cap relative to the second end cap. Thus, the specimen is not exposed to any rotational forces when the expansion cylinder is rotated to create the expansion forces.

The specimen preferably is configured as a rod and has threads formed on the first and second ends of the rod for being threadedly attached to the end caps. One or more grooves are formed circumferentially around the mid-section of the rod in the area that is to be tested. For example, a groove can be formed in a weld zone that is formed in the specimen and the strength characteristics of the weld zone will be tested. Likewise, the heat affected zone that is adjacent to a weld zone may have a groove formed in it and the material properties of the heat affected zone can be tested. Preferably the groove is a v-notch.

In accordance with one embodiment, a first stress-strain sensor is disposed on the specimen for measuring stress-strain in the specimen and at least one dummy sensor is disposed on the exterior of the frame. A bridge circuit interconnects the first stress-strain sensor and the dummy sensor or sensors so that the electrical characteristics of the bridge circuit correspond to the stress-strain experienced by the specimen and the dummy sensor compensates for stress-strain caused by environmental changes. There are preferably three dummy sensors in a full bridge circuit.

One may also apply one or more strain gages to the frame itself to measure the stress-strain experienced by the frame. Again, the sensors may be arranged in a bridge circuit so as to compensate for environmental changes. In one embodiment, four gage resistors are mounted on the outside of a compression column of the frame. Two of the gage resistors are mounted vertically and two gage resistors are mounted horizontally, where vertical is defined as parallel to the direction of the stress-strain forces produced by the frame and horizontal is perpendicular to vertical. The four gages are mounted in a Full Poisson Bridge such that a voltmeter in the bridge reads voltages that correspond to the voltage drops across the four gages and the output of the voltmeter is calibrated to correspond to vertical forces applied to the compression column. When is use, the vertical force on the compression column is the same as the tension force being applied to the specimen. By monitoring the vertical force on the compression column, the tension force is indirectly monitored and the stress-strain on the specimen may be calculated based on the monitored vertical force.

The first and second end caps, the specimen, the adjusting mechanism and the compression element may be compactly configured so that they may be easily disposed in an environmental chamber. Multiple testing devices may be placed in the environmental chamber at the same time to test multiple specimens. The environmental chamber exposes the specimen to extreme environments, such as a hydrogen environment at pressures typically in the range of 3,000 psi, but much higher pressures may be used. For example, a pressure of about 10,000 psi could be used. In this configuration, multiple specimens may be tested conveniently and accurately in a small pressurized gas chamber.

BRIEF DESCRIPTION OF THE DRAWINGS

The embodiments may best be understood by reference to the attached drawings in which FIG. 1 schematically represents a stress-strain test frame inside an environmental chamber;

FIG. 5 is a cross-sectional view of the test frame of FIG. 3;

FIG. 5A-A is a cross-sectional view taken through line A-A in FIG. 5;

FIG. 5B-B is a cross-sectional view of the test frame taken through line B-B in FIG. 5;

FIG. 5C-C is a cross-sectional view taken through line C-C in FIG. 5;

FIG. 6A is an end view of a tubular cap;

FIG. 6B is a side cross-sectional view of the tubular cap; and

FIG. 6C is an opposite end view of the tubular cap;

FIG. 8 is a side cross-sectional view of a cylindrical compression column and;

FIG. 8A-A is a cross-sectional view taken through line A-A in FIG. 8;

FIG. 9A is an end view of a tubular cap;

FIG. 9B is a side cross-sectional view of a tubular cap and;

FIG. 9C is an opposite end view of the tubular cap.

DETAILED DESCRIPTION

Figure 1:
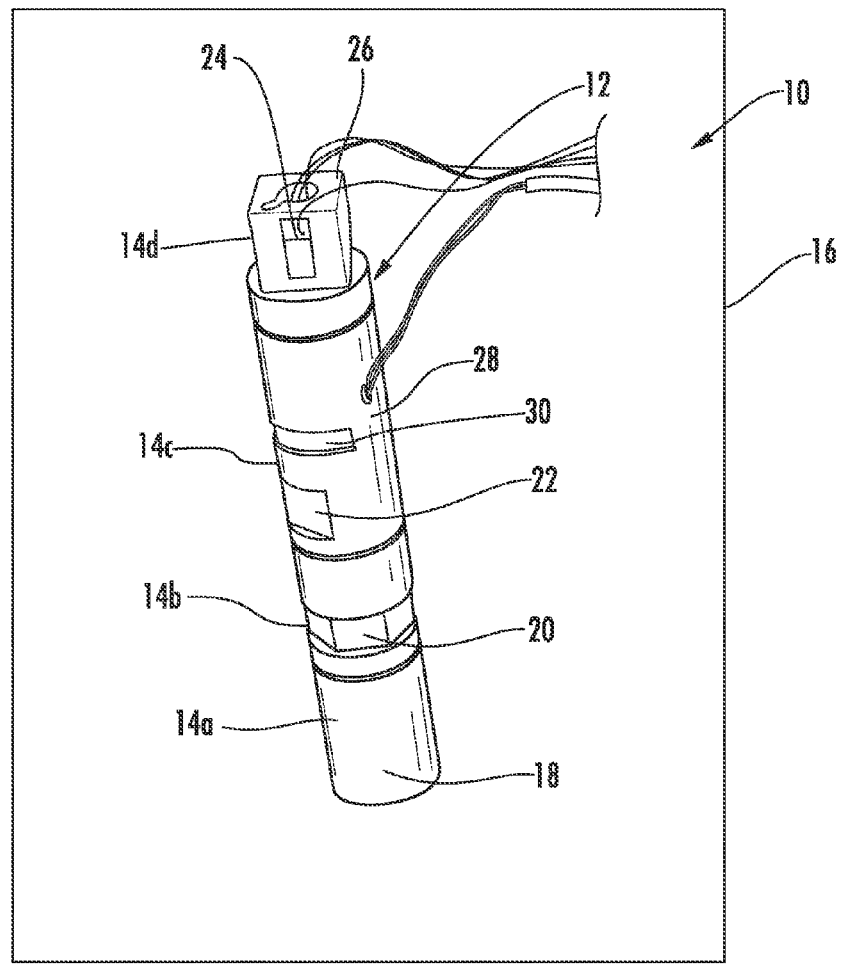

Referring now to FIG. 1, there is shown a stress-strain testing apparatus 10. A test frame 12 is shown in a three dimensional representation and an environmental chamber 16 is shown diagrammatically as a box. In operation, the stress-strain test frame 12 is used to impose a stretch or stress-strain on a specimen contained within the frame 12 and the environmental chamber 16 is used to expose the specimen within the test frame to a controlled atmosphere. For example, the atmosphere within the chamber 16 may be pressurized hydrogen at 3,000 psi to 10,000 psi, or even higher.

The test frame 12 in this embodiment has four elements. A tubular first end cap 14A, a stress-strain adjusting cylinder 14B, a tubular compression column 14C and a second end cap 14D. The first end cap 14A includes a pair of flats 18 and the cylinder 14B includes a pair of flats 20. Also, the compression column 14C includes flats 22. Although only flats 18, 20 and 22 are shown in FIG. 1, it will be appreciated that at least one additional flat is provided on the opposite side of each of these elements so that the cap 14A, cylinder 14B and column 14C may be engaged by a tool, vice or other holding mechanism and the elements may be rotated about their center axis with respect to one another. In operation, in order to impose a stress-strain on a specimen within the test frame 12, the compression column 14C and the first end cap 14A are held stationary using the flats 18 and 22. Then, the stress-strain adjusting cylinder 14B is rotated using flats 20 to either extend or retract the length of the test frame 12 and thereby either increase or decrease stress-strain on the specimen contained within the frame 12.

Figure 2:
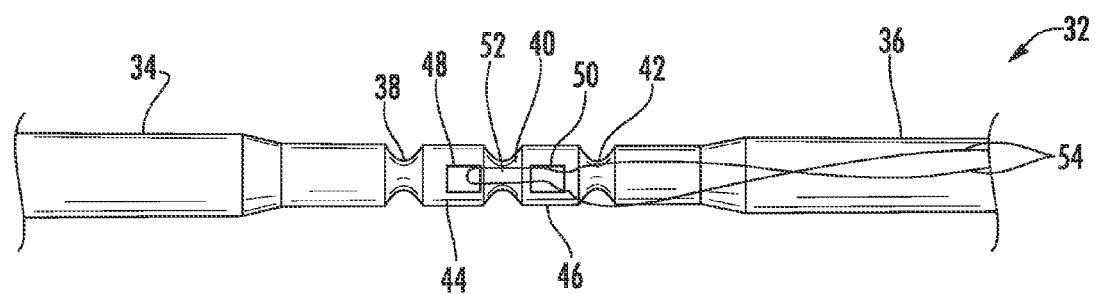
FIG. 2 is an enlarged view of the center of a test specimen.

A partial view of a test specimen 32 is shown in FIG. 2. The specimen 32 is held within the test frame 12 described above and is preferably stress-strained by exerting force on the opposite ends 34 and 36 of the specimen 32. In the center of the specimen 32, three grooves 38, 40 and 42 are disposed circumferentially. In this embodiment, the groove 40 is machined in the specimen 32 at a weld zone. The specimen 32 had been previously welded in the area of the groove 40 for the purpose of testing the strength of the weld. The grooves 38 and 42 are located in an area of the specimen that is not a part of the weld zone, but is a part of the heat affected zones adjacent to the weld zone. Thus, groove 40 is in a weld zone and grooves 38 and 42 are in heat affected zones. Landings 44 and 46 are disposed on opposite sides of the groove 40 and a strain gage resistor 52 is mounted across the landings 44 and 46. A contact pad 48 is attached to the landing 44 and another contact pad 50 is attached to the landing 46. The contact pads 48, 50 are secured to the strain gage resistor 52 that extends between the two landings 44 and 46 and across the groove 40. Lead wires 54 extend away from the strain gage resistor 52 and are directed to external electronics for determining stress-strain across the groove 40. As the specimen 32 is placed under different forces, such as a tensile force applied by the test frame 12 or gas pressure exposure inside the chamber 16, the induced stress-strain will be measured by the strain gage resistor 52 and monitored through the lead lines 54.

Referring now to both FIGS. 1 and 2, the strain gage resistor 52 is connected in a bridge to multiple dummy gages, for example, three dummy gages that are mounted on end cap 14D shown in FIG. 1. Two such dummy gages 24 and 26 are shown in FIG. 1. The strain gage resistor 52 and dummy gages are calibrated before the specimen 32 is inserted into the test frame 12. Then, as the test frame 12 is adjusted to apply force to the specimen 32, the stress-strain reported by the strain gage resistor 52 is monitored. Later, when the specimen 32 and test frame 12 are placed in the chamber 16 and exposed to an environment, such as high pressure hydrogen, the stress-strain reported by the gage resistor 52 is constantly monitored while the multiple dummy gages, such as gages 24 and 26, function to measure and allow compensation for environmental effects on the gage resistor 52 itself. Thus, the gage resistor 52 will accurately monitor the changing stress-strain on the specimen 32 across the groove 40 and will minimize the stress-strains in the gage resistor 52 itself caused by a changing environment. The dummy gages 24 and 26 will experience the same changing environment and will automatically compensate for the changing environment and avoid misreporting the stress-strain actually experienced by the specimen 32. Also, the compression column 14C may be monitored for stress-strain as well. For example, four strain gages may be mounted on the exterior of the column 14C at 90 degree angles around the circumference of the column 14C. Strain gages 28 and 30 are shown in FIG. 1 mounted on the exterior of the compression column 14C and two additional such strain gages are hidden from view. The operation of these gages 28 and 30 are described with reference to FIGS. 10A and 10B in which gages 28 and 30 are represented by gages 102 and 104 for example.

Figure 3:
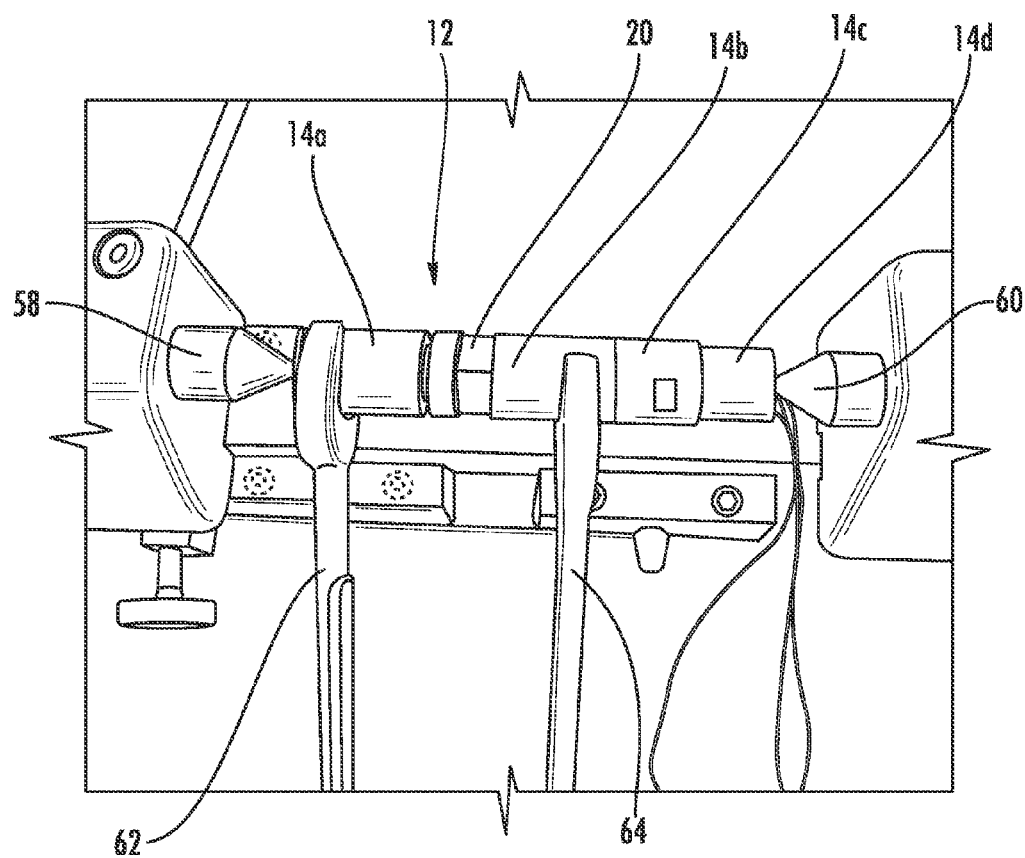
FIG. 3 shows the stress-strain test frame held for imposing a stress-strain on a test specimen.

Referring now to FIG. 3, the test frame 12 is shown in a pair of conical holders 58 and 60 in position for adjusting the stress-strain on the specimen 32 located within the frame 12. The holders 58 and 60 allow the test frame 12 to extend or retract. In this particular embodiment, the first end cap 14A and the compression column 14C are shown held by fixed wrenches 62 and 64 that are engaging the flats 18 and 22 on their respective parts. Thus, the wrenches 62 and 64 hold the cap 14A and the compression column 14C in a stationary position. It will be appreciated that the fixed wrenches 62 and 64 could provide all necessary support for the test frame 12 and the holders 58 and 60 could be eliminated in that embodiment. While the wrenches 62 and 64 are engaged, the stress-strain adjusting cylinder 14B may be rotated using a wrench or other tool which engages the flats 20. If the cylinder 14B is rotated in a counter-clockwise direction, the length of the test frame 12 is extended and the specimen 32 within the test frame 12 experiences a stress-strain. If the cylinder 14B is rotated in a clockwise direction, the test frame 12 retracts in length and reduces the stretching forces on the specimen 32. Thus, a desired stress-strain may be applied by the frame 12 to the specimen 32 by rotating the stress-strain adjusting cylinder 14B.

Figure 4:
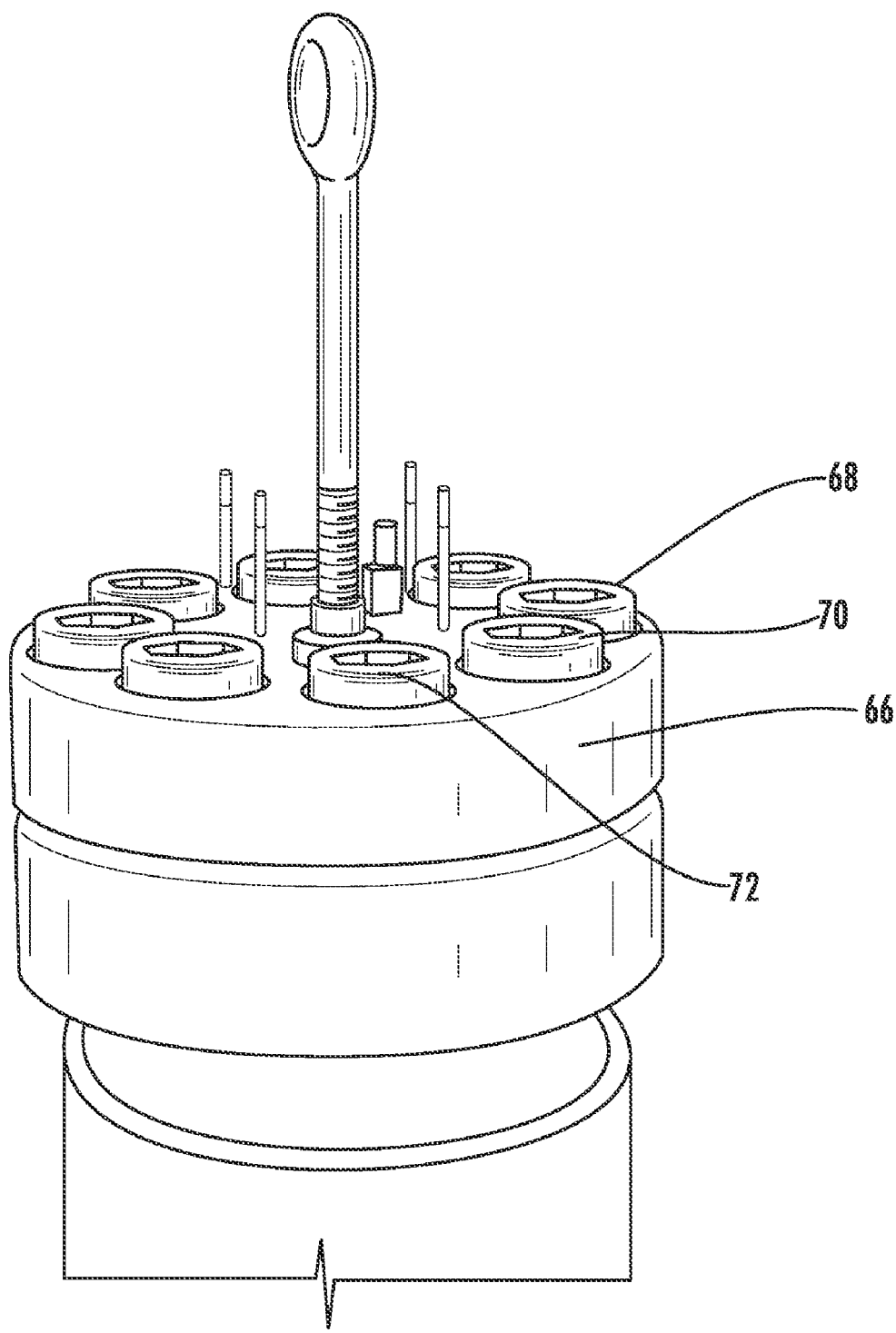
FIG. 4 is a perspective illustration of a rack for holding multiple test frames in an environmental chamber.

Referring to FIG. 4, a carrier 66 is shown that includes multiple racks, such as racks 68, 70 and 72. In practice, each of the racks will contain and carry a test frame 12 loaded with a specimen 32. Then, the carrier 66 may be placed inside the environmental chamber 16 and multiple specimens 32 may be exposed to the same environment and tested simultaneously. Each of the specimens will include a strain gage resistor 52 to monitor the stress-strain that is imposed upon the test zone in the specimen as it is exposed to the environment.

Referring to FIG. 2, it will be appreciated that the strain gage resistor 52 could alternatively be placed across groove 38 or groove 42 and the stress-strain experienced by the heat affected zones of the specimen 32 may be monitored instead of the weld zone. In such case, the weld zone may not be grooved if desired so that the point of failure, if any, will occur in the heat affected zones within the grooves 38 and 42. Similarly, a specimen 32 without a weld could be tested by providing a groove in the specimen 32 and placing the strain gage resistor 52 across the groove in a zone that had not been welded.

Additional details of the embodiment described herein are shown in FIGS. 5-9. It will be understood that this particular detailed embodiment is just one exemplary embodiment and should not be construed as limiting. As detailed in the exemplary embodiment, threads are used as fasteners to engage elements of the assembled frame 12 with each other and/or to engage elements of the assembled frame to sections of the specimen 32. However, it should be understood that other types of fasteners may be used.

Referring to FIGS. 5, 5AA, 5BB and 5CC, details of the assembled frame 12 are shown. The specimen 32 is shown mounted within the frame 12 and threads 66 are formed on the specimen end 34 and matching threads 68 are formed in the end cap 14A. Likewise, threads 80 are formed on the other end 36 on the specimen 32, and matching threads 78 are formed in the cap 14D. Thus, each end 34, 36 of specimen 32 may be threadedly engaged with one of the end caps 14A and 14D with the elements 14B and 14C disposed between the caps 14A and 14D.

The stress-strain adjustment cylinder 14B is threadedly secured within the end of cap 14A. Thus, exterior threads 72 on the cylinder 14B engage with interior threads 70 in the cap 14A. Mating shoulders 74 and 76 are formed on the ends of the compression column 14B and adjusting cylinder 14C, respectively. Thus, the column 14C and the adjusting cylinder 14B are concentrically aligned and held in a concentric abutting position by the shoulders 74 and 76. Likewise, mating shoulders 82 and 84 are formed on the compression column 14C and end cap 14D, respectively, such that the two elements again are held in an aligned concentric position by the shoulders 82 and 84

To assemble the frame, the end 34 of the specimen 32 is first threadedly secured into the end cap 14A. Then, the stress-strain adjustment cylinder 14B is threadedly secured into the end cap 14A enclosing concentrically the specimen 32. The compression column 14C is fitted against the cylinder 14B causing the shoulders 74 and 76 to mate and hold the column in position for continued assembly. Finally, the end cap 14D is threaded onto the end 36 of specimen 32 until the shoulders 82 and 84 engage thereby capturing and holding the compression column 14C.

Once the frame 12 is assembled, a desired stress-strain is imposed on the specimen 32 by rotating the cylinder 14B backwards (counter-clockwise), for example by using a wrench on flats 20, such that it is threaded out of the end cap 14A. As the cylinder 14B is threaded backwards, the cap 14A and the compression column 14C are held stationary by the wrenches on flats 18 and 22. The cylinder 14B engages the compression column 14C at the interface of the shoulders 74 and 76 and the cylinder 14B applies a compression force against the compression column 14C through the shoulders 74 and 76. The threads on the adjusting cylinder 14B function as both a fastener and an adjustment mechanism for applying and adjusting a stress-strain on the specimen 32. A dry lubricant is preferably provided between the shoulders 74 and 76 and also between the threads 70 and 72 to reduce galling. The compression force applied to the compression column 14C is transmitted to the end cap 14D and then to the end 36 of the specimen 32. Thus, pressure or force is applied in opposite directions to the ends 34 and 36 of the specimen 32 and a stress-strain is imposed on the specimen 32. As previously described, the specimen includes a strain gage resistor 52 that reports the stress-strain on the specimen 32 as the adjusting cylinder 14B is rotated. Thus, a desired stress-strain may be imposed on the specimen.

In FIG. 5, the grooves and the strain gage have been omitted from the specimen 32 for purposes of clarity of illustration. However, it will be understood that a strain gage and the corresponding lead lines may be provided as previously discussed, and if desired, the grooves may be provided as well.

Figure 7C:
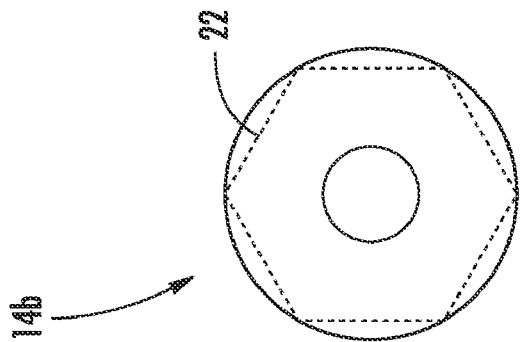
FIG. 7C is an opposite end view of the stress-strain adjusting cylinder.
Figure 7B:
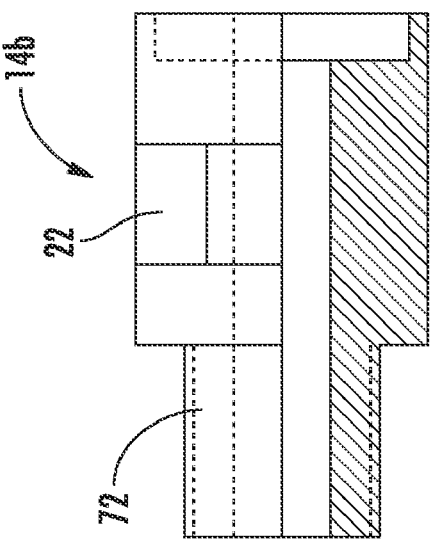
FIG. 7B is a side cross-sectional view of the stress-strain adjusting cylinder.
Figure 7A:
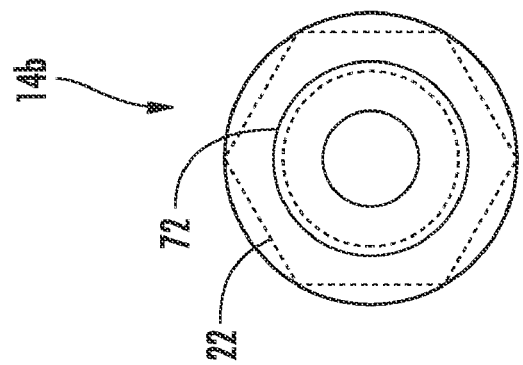
FIG. 7A is an end view of a stress-strain adjusting cylinder.

FIG. 6B shows a cross-sectional view of the first end cap 14A and FIG. 6A and FIG. 6C show views of the opposite ends of the first end cap 14A. In the exemplary embodiment illustrated, the threads 66 are preferably ¼ inch in diameter and have a thread of 28 UNF-2B. The threads 70 are preferably ½ inch diameter –28 UNEF-2B. The flats 18 are preferably ⅝ of an inch apart. The stress-strain adjusting cylinder 14B is shown in cross-section in FIG. 7B and end views of the cylinder 14B are shown in FIGS. 7A and 7C. The threads 72 on the cylinder 14B are preferably ½ an inch in diameter and 28 UNEF-2B. The flats 22 form a hexagonal, nut-shape on the exterior of the cap 14A and have a diameter of ⅝ of an inch.

Further details of the compression column 14C are shown in FIG. 8. The two flats 22 in the compression column 14C are preferably ⅝ of an inch apart and 0.30 inches wide. Four holes 92 are provided through the walls of the column 14C to allow hydrogen or other gases to circulate through the column 14C and into the area of the specimen within the column. As shown in FIG. 8A, the holes are preferably 1/16 of an inch in diameter and are equally spaced apart around the circumference of the compression column 14C. Thus, each hole is oriented at 90 degrees with respect to adjacent holes.

A detailed view of the second end cap 14D is shown in FIGS. 9A-C. FIG. 9B is a cross-sectional view and FIGS. 9A and 9C are the two end views. As shown, there are four holes 94 formed in the end cap 14D in a direction parallel to the center axis of the cap 14D. The holes are preferably 1/16 of an inch in diameter and are spaced along an imaginary circle on a planar surface of the end cap and are spaced apart by 90 degrees. The holes through the end cap provide a passage for gases and the lead wires 54 extending from the strain gage resistor 52 (not shown) so that the lead wires 54 may pass out of the frame 12 and be attached to appropriate instrumentation. The thickness of the shoulder 92 is approximately 0.09 inches and the threads 78 are ¼ inch –28 UNF-2B threads.

In an alternate embodiment, the strain gages may be mounted only on the frame 12 and not on the specimen 32. In this alternate embodiment, the stress-strain is measured on the frame 12 and this stress-strain is an indirect measurement of the stress-strain placed on the specimen by the frame. For example, as shown in FIG. 10, four strain gages 102, 104, 106 and 108 are placed on the outside of a compression column 110, which corresponds to the compression column 14c discussed above. Each of these gages included a gage sensor that measures stress-strain in substantially only one direction, such as gage resistor 52 discussed above. The gages 102 and 106 are oriented vertically on the column 110 with vertically being defined in this case as parallel to the direction in which the column 110 places a tension force on the specimen 32. In this case, the direction of the tension forces applied by column 110 is indicated by arrows 112 and 114. Thus gages 102 and 106 measure compression stress-strain on the column 110 and these compression stress-strain measurements may be calibrated to actual tension forces applied to a specimen by the column 110. Thus, by reading the stress-strain on gages 102 and 106, the tension force on a specimen within the column 110 may be determined.

The strain gages 104 and 108 are mounted horizontally and any changes in the stress-strain measured by gages 104 and 108 are also caused by compression forces on compression column 110. Thus, the outputs from gages 104 and 108 may also be used to monitor the vertical force applied to the compression column. When the compression force increases, the circumference of the column will increase and place and increased stress-strain on the horizontal strain gages 104 and 108. In response to increased vertical compression force on the compression column, the length of the compression column 110 decreases and reduces the stress-strain on the vertical strain gages 102 and 106. So, in response to increased vertical forces on the column, the resistance of the vertical gages 102 and 106 decreases and the resistance of the horizontal gages 104 and 108 increases.

Figures 10A, 10B:
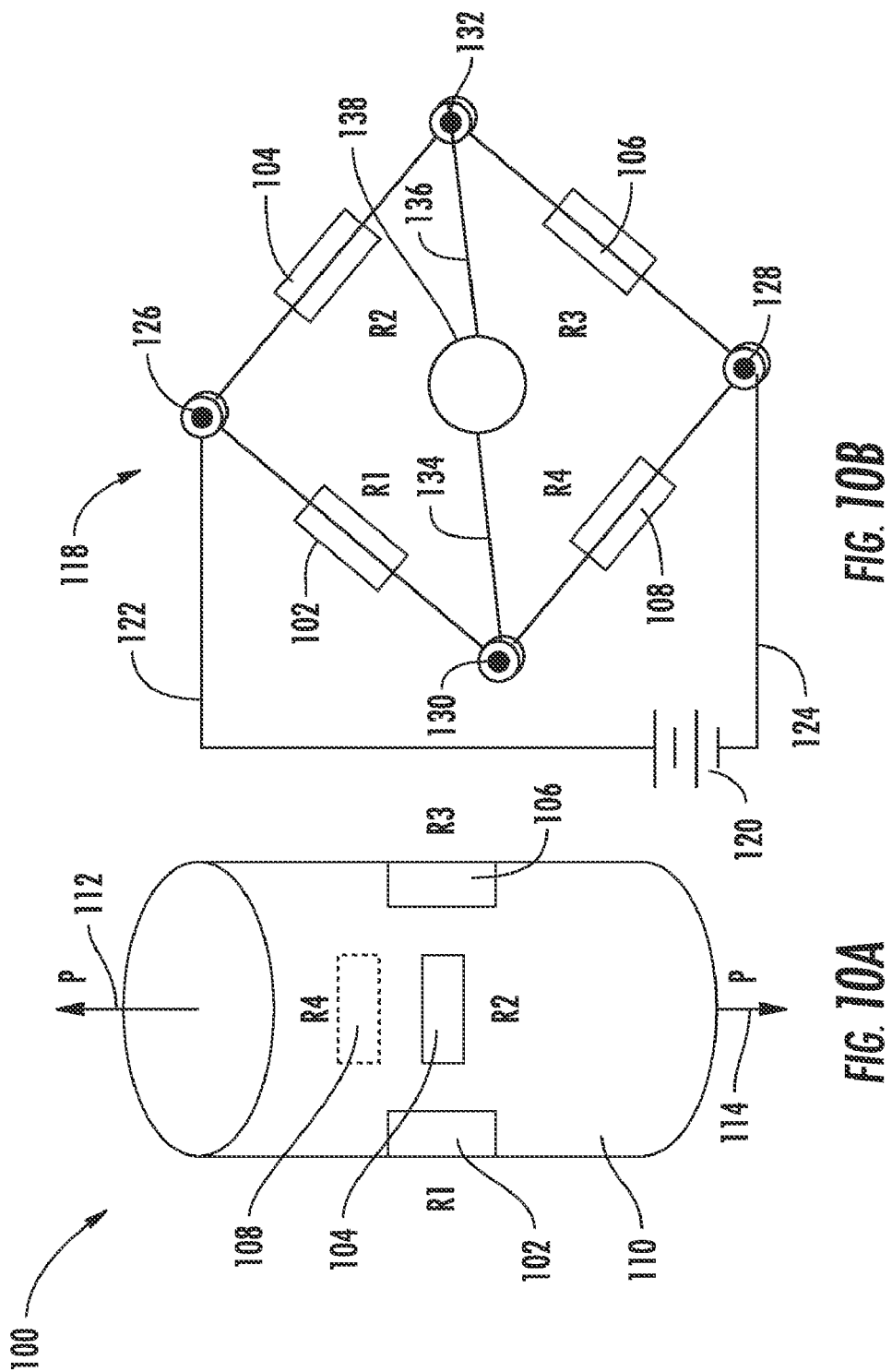
FIG. 10a is a diagrammatic view of an alternate embodiment in which strain gages are placed on the frame to indirectly measure stress-strain on a specimen.
FIG. 10b is an electrical diagram showing how the four strain gages shown in FIG. 10a are connected in a full Poisson bridge.

FIG. 10B shows a circuit diagram illustrating how the four gages 102, 104, 106 and 108 are interconnected electrically. This particular interconnection is an efficient and convenient way to read and interpret the gages, but it will be understood that each individual gage could be monitored separately, if desired, and the same or similar results could be obtained by calculations performed manually or automatically with a digital computer, for example. In FIG. 10B, a fixed voltage source 120 is provided, which may be a battery or other electrical power source and it is designed to provide a stable voltage. If desired, a constant voltage circuit may be included as part of source 120 so that the voltage output of source 120 is held constant even under changing conditions of the source 120 and the environment.

The source 120 is connected by lines 122 and 124 to apply a voltage potential across junctions 126 and 128. The vertical gage 102 is connected between junction 126 and a junction 130, and the horizontal gage 108 is connected between junctions 130 and 128. Likewise horizontal gage 104 is connected between junction 126 and a junction 132, and vertical gage 106 is connected between the junctions 132 and 128. Thus two series circuit paths are formed between junctions 126 and 128, and each circuit path includes one horizontal gage in series with a vertical gage. A voltage meter 138 is connected between junctions 130 and 132 by lines 134 and 136 to complete the Full Poisson Bridge.

When a vertical compression is placed on the column, the vertical gages 102 and 106 experience reduced stress-strain in the vertical direction and their sensor value changes (eg., the resistance of a sensor resistor changes). Assuming the vertical strain gages 102 and 106 were pre-stressed in tension in the vertical direction, then vertical compression forces will reduce the tension in gages 102 and 106 and their resistance will decrease. The horizontal gages are also subjected to changed stress-strain, so their sensor values (eg., resistance) changes in response. In this case the resistance of gages 104 and 108 increases in response to increases in vertical compression forces. Considering the bridge in FIG. 10B, assuming the resistance of gages 102 and 106 decreased, and the resistance of gages 104 and 108 increased, then the voltage drop across gages 102 and 106 decreases and the voltage drop across gages 104 and 106 increases. Thus the voltage change experienced at the voltmeter 138 is equal to the collective changes in voltage drop across gages 102, 104, 106 and 108, which corresponds to the change in stress-strain in the vertical direction. Thus, the voltmeter 138 produces an output that is a measure of the vertical stress-strain on the column 110.

The voltmeter 138 output is calibrated to correspond to the stress-strain on the column caused by the vertical forces applied to the column 110. To calibrate the voltmeter 138 various different vertical forces are applied to the column 110 and the voltage recorded by the voltmeter 138 is recorded in a lookup table that is later used to interpret the output of the voltmeter 138. If the voltage on the lookup table and the voltage on the voltmeter 138 cannot be identically associated, then interpolation is used to determine the vertical compression force from a voltmeter reading. Alternatively, the values in the lookup table can be used to create a continuous calibration curve of create a calibration function, either of which may be used in a manner similar to the use of the lookup table to determine the compression force on column 110 which is equal to the vertical tension force being applied to the specimen.

Figure 11:
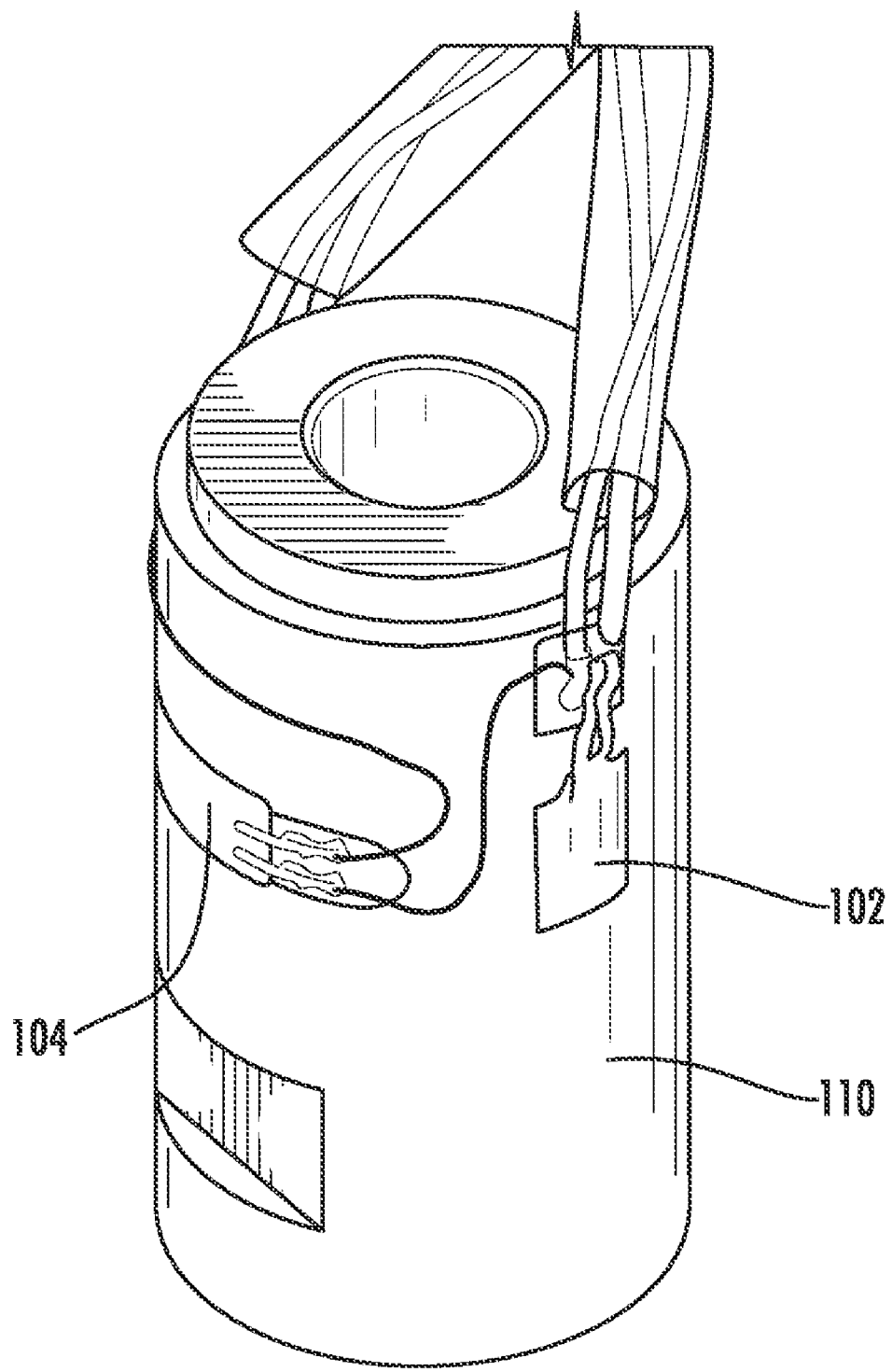
FIG. 11 is a perspective view of a compression column showing one vertically mounted strain gage and one horizontally mounted strain gage.
Figure 12:
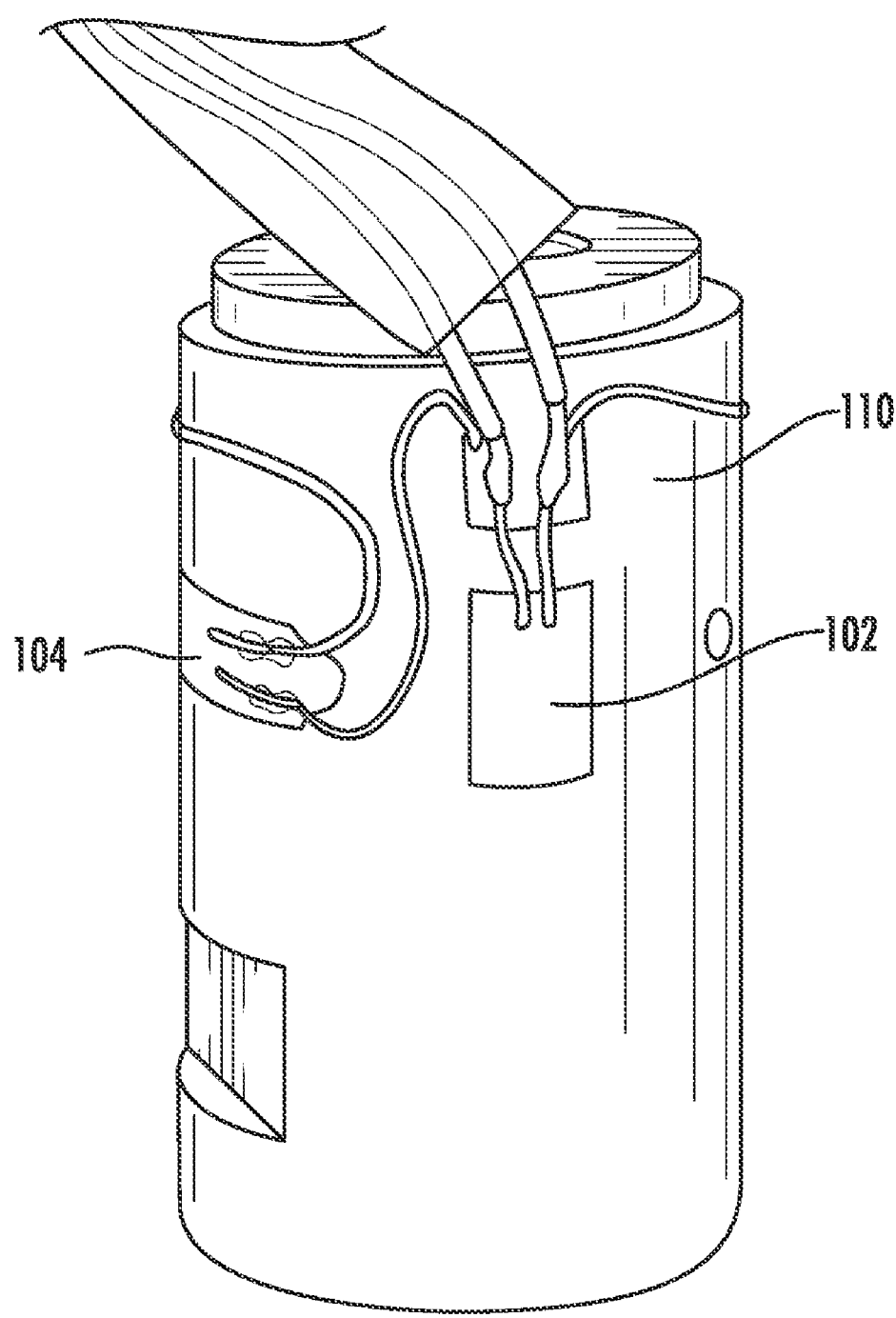
FIG. 12 is a perspective view of a compression column showing one vertically mounted strain gage.
Figure 13:
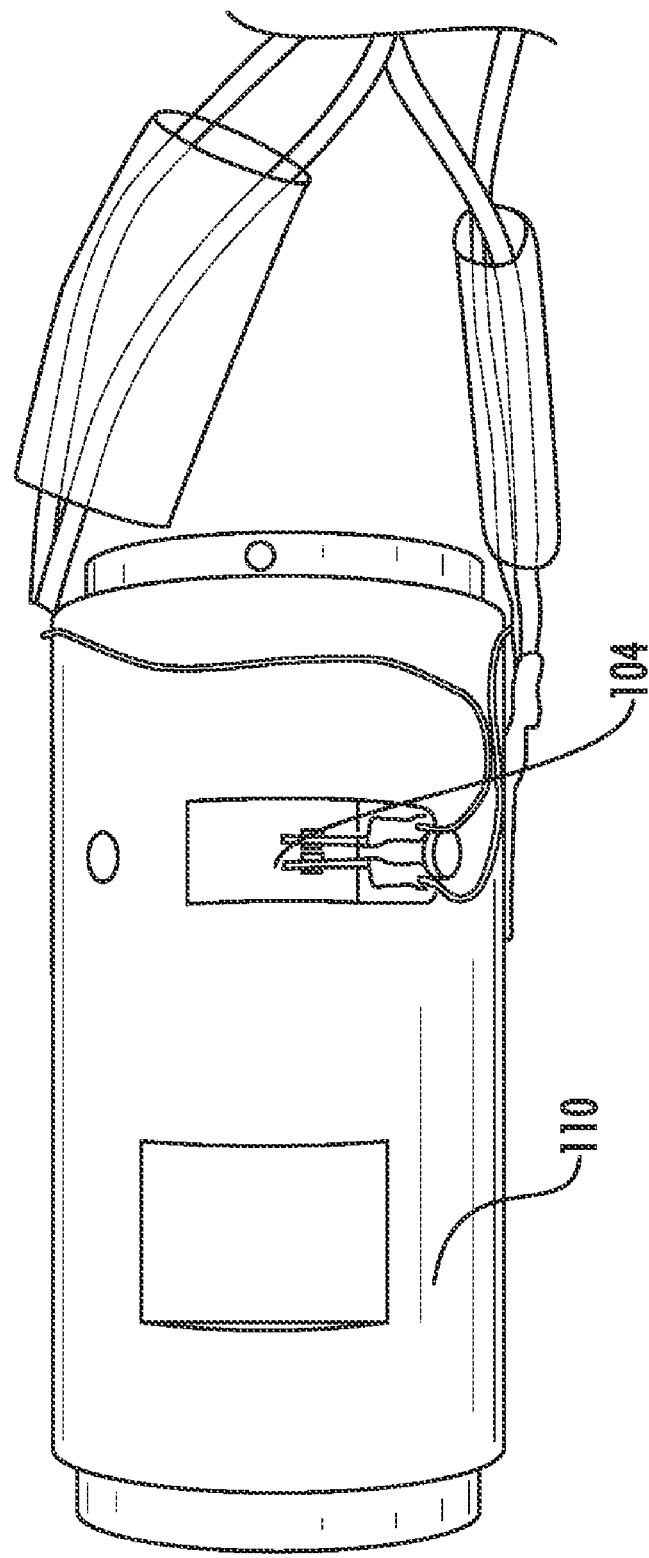
FIG. 13 is a perspective view of a compression column showing one horizontally mounted strain gage.

FIGS. 11, 12 and 13 are perspective views that more realistically portray the mounting of the gages 102-108 on the compression column 110 and more realistically portray the electrical interconnections. However, the electrical interconnections shown in FIGS. 11, 12 and 13 are the same as shown in FIG. 10B.

In all embodiments, the materials used for the test frame 12 will vary depending upon the application. In most embodiments high strength stainless steel will be suitable, but any material that is substantially inert to attack from the harsh environment would be suitable. For use in high pressure hydrogen environments, stainless steel is appropriate as the material for the frame 12 because it is substantially inert from attack by hydrogen, whereas other steels, such as non-stainless carbon steels are not. In other embodiments, ceramic materials may be used and such materials are most useful when testing other ceramic materials. While specific embodiments have been described or mentioned in this application, it will be understood that the invention is capable of numerous re-arrangements, modifications and substitutions of parts without departing from the scope of the invention as defined by the appended claims.

What is claimed is:

1. A stress-strain testing apparatus for use in testing a specimen under conditions of stress-strain comprising:
   a. a frame including:
      i. first and second end caps; and
      ii. an adjusting mechanism disposed between the first and second end caps, the adjusting mechanism extending apart and applying opposed outward compressive forces on the first and second end caps, the specimen being attached between the first and second end caps so that the opposed outward compressive forces on the end caps apply a tension force on the specimen and impose a stress-strain on the specimen; and
   b. a strain gage attached to measure stress-strain being applied by the frame to the specimen.

2. The apparatus of claim 1 wherein the strain gage is attached to the frame to measure stress-strain on the frame and thereby indirectly measure the stress strain on the specimen.

3. The apparatus of claim 1 wherein the strain gage is attached to the specimen to directly measure the stress-strain on the specimen and thereby indirectly measure the stress-strain being applied by the frame.

4. The apparatus of claim 1 wherein the strain gage comprises:
   a. first, second, third and fourth gage resistors with the first and third gage resistors being mounted vertically on the frame, with the second and fourth gage resistors being mounted horizontally on the frame, and where vertical is defined as parallel to the direction of the opposed forces and horizontal is defined as perpendicular to the direction of the opposed forces, and
   b. an electrical circuit connected to the gage resistors for measuring changes in the resistances of the four gage resistors.

5. The apparatus of claim 1 wherein the strain gage comprises:
   a. first, second, third and fourth gages with the first and third gages being mounted vertically on the frame, and where vertical is defined as parallel to the direction of the opposed forces and horizontal is defined as perpendicular to the direction of the opposed forces, and
   b. an electrical circuit connecting the gages in a Full Poisson Bridge and applying a voltage across the first, second, third and fourth gages, the electrical circuit including a voltmeter connected to measure a voltage corresponding to the voltages across the gages, the electrical circuit being configured such that the voltage measured by the voltmeter corresponds to stress-strain on the column in the vertical direction.

6. The apparatus of claim 1 wherein the frame further comprises a compression column having a tubular shape and having an interior dimensioned to receive the specimen and allow it to pass through the compression column and attach to the first and second end caps.

7. The apparatus of claim 1 further comprising at least one strain gage disposed on the frame for sensing stress-strain experienced by the frame.

8. The apparatus of claim 1 further comprising an environmental chamber containing the frame and the strain gage and exposing the frame and strain gage to extreme environments for testing the specimen.

9. The apparatus of claim 1 further comprising an environmental chamber containing the frame and the strain gage and exposing the frame and strain gage to extreme environments of high pressure hydrogen up to about 10,000 psi for testing the specimen.

10. The apparatus of claim 1 further comprising holes in one or more of the frame and the second end caps for exposing the specimen to gas surrounding the frame and end caps.

11. A stress-strain testing apparatus for use in testing a specimen under conditions of stress-strain comprising:
   a. a frame including:
      i. first and second end caps; and
      ii. an adjusting mechanism disposed between the first and second end caps, the adjusting mechanism for extending apart and applying opposed forces on the first and second end caps, the specimen being attached between the first and second end caps and having a stress-strain imposed on the specimen by the opposed forces being applied to the first and second end caps by the adjusting mechanism; and
   b. a strain gage attached to measure stress-strain being applied by the frame to the specimen;
   wherein
   the frame further comprises an adjusting cylinder having threads formed on the adjusting cylinder;
   the first end cap further comprises threads formed on the first end cap for mating with the threads of the adjusting cylinder so that the end cap is threadedly secured to the adjusting cylinder and so that the adjusting cylinder may be rotated relative to the first end cap to move the adjusting cylinder away from the first end cap, and
   the frame being configured and disposed to impose opposing, forces on the first and second end caps and impose a stress-strain on the specimen in response to the movement of the adjusting cylinder.

12. The apparatus of claim 11 wherein:
   a. the frame further comprises
      i. a compression column having a tubular shape and having an interior dimensioned to receive the specimen and allow it to pass through the compression column and attach to the first and second end caps,
      ii. first and second end faces formed on the compression column, the first face being configured and disposed to apply an opposing force to the second end cap, and
      iii. an adjusting cylinder having a tubular shape and having an interior dimensioned to receive the specimen and allow it to pass through the adjusting cylinder, the adjusting cylinder having a first end configured to engage and mate with the second end face of the compression column, the adjusting cylinder having a second end and having threads formed on the second end;
   b. the first end cap further comprising threads formed on the first end cap configured for mating and attaching to the threads of the adjusting cylinder, the first end cap being secured to the adjusting cylinder by the threads of the first end cap and the threads of the adjusting cylinder so that rotation of the adjusting cylinder in one direction will move the first end cap and the adjusting cylinder apart thereby applying compression forces on the compression column and the adjusting cylinder and thereby apply the opposing forces to the first and second end caps.

13. A stress-strain testing apparatus for use in testing a specimen under conditions of stress-strain comprising:
   a. a frame including:
      i. first and second end caps; and
      ii. an adjusting mechanism disposed between the first and second end caps, the adjusting mechanism for extending apart and applying opposed forces on the first and second end caps, the specimen being attached between the first and second end caps and having a stress-strain imposed on the specimen by the opposed forces being applied to the first and second end caps by the adjusting mechanism;
   b. a strain gage attached to measure stress-strain being applied by the frame to the specimen, the strain gage including:
      i. a first stress-strain sensor disposed on the specimen,
      ii. at least one dummy stress-strain sensor disposed on the exterior of the frame, and
      iii. abridge circuit interconnecting the first stress-strain sensor and the dummy stress-strain sensor so that electrical characteristics of the bridge circuit correspond to the stress-strain experienced by the specimen and the dummy sensor compensates for stress-strain caused by environmental changes.

14. A stress-strain testing apparatus comprising:
   a. a first end cap having first and second fasteners;
   b. a specimen having first and second ends and a midsection, the first end being fastened to the first fastener on the first end cap;
   c. an adjusting mechanism attached to the first end cap by the second fastener and being configured to extend and retract in response to external force;
   d. a compression element abutting the adjusting mechanism for carrying compression forces caused by extending the adjusting mechanism;
   e. a second end cap having a third fastener, the second end of the specimen being attached to the second end cap by the third fastener;
   f. the first end cap, the adjusting mechanism, the compression element and the second end cap being configured to compress together in response to extending the adjusting mechanism and imposing a tension force on the specimen and thereby causing stress-strain in the specimen that is measured by the strain gage; and
   g. a strain gage disposed for measuring the tension force produced by the first end cap, the adjusting mechanism, the compression element and the second end cap and applied to the specimen.

15. The apparatus of claim 14 further comprising an environmental chamber containing and exposing to extreme environments the first end cap, the specimen, the adjusting mechanism, the compression element, the second end cap and the strain gage.

16. The apparatus of claim 14 further comprising at least one strain gage mounted on the exterior of at least one of the adjusting mechanism or the compression element for measuring stress-strain.

17. The apparatus of claim 14 wherein the specimen comprises:
   a. a rod of specimen material having first and second ends and a midsection;
   b. threads formed on the first and second ends of the rod; and c. a groove formed circumferentially around the midsection of the rod.

18. The apparatus of claim 14:
   a. wherein the specimen comprises:
      i. a rod of specimen material having first and second ends and a midsection; and
      ii. a weld zone formed in the midsection of the rod; and
   b. wherein the strain gage is disposed across the weld zone to sense the stress-strain in the weld zone.

19. The apparatus of claim 14:
   a. wherein the specimen comprises:
      i. a rod of specimen material having first and second ends and a midsection;
      ii. a weld zone formed in the midsection of the rod;
      iii. threads formed on the first and second ends of the rod; and
      iv. a groove formed circumferentially around the midsection of the rod in the weld zone; and
   b. wherein the strain gage is disposed across the groove to sense the stress-strain in the weld zone.

20. The apparatus of claim 14:
   a. wherein the specimen comprises:
      i. a rod of specimen material having first and second ends and a midsection;
      ii. a heat affected zone formed in the midsection of the rod;
      iii. threads formed on the first and second ends of the rod; and
      iv. a groove formed circumferentially around the midsection of the rod in the heat affected zone; and
   b. wherein the strain gage is disposed across the groove to sense the stress-strain in the heat affected zone.

21. A stress-strain testing apparatus comprising:
   a. a first end cap having a smaller threaded receiver and a larger threaded receiver coaxially aligned;
   b. a specimen having first and second threaded ends and a midsection, the first end being threaded into the smaller threaded receiver on the first end cap;
   c. an adjusting mechanism having:
      i. a first passage disposed about the specimen,
      ii. a threaded end that is threaded into the larger threaded receiver of the first end cap and is configured to cause expansion and compression forces when rotated in one direction within the larger threaded receiver,
      iii. a second end,
      iv. a shoulder formed on the second end;
   d. a compression column having:
      i. first and second ends;
      ii. a second passage disposed about the specimen,
      iii. a second shoulder formed on the first end of the compression column and abutting the first shoulder of the adjusting mechanism, the first and second shoulders being configured to provide a sliding interface between the first and second shoulders that allows rotational sliding motion, the first and second shoulders being configured to transmit compression forces caused by expansion of the adjusting mechanism;
   e. a strain gage disposed at least in part on the midsection of the specimen for measuring stress-strain of the specimen;
   f. a second end cap having a third threaded receiver, the second treaded end of the specimen being threaded into the third receiver in the second end cap;
   g. the first end cap, the adjusting mechanism, the compression column and the second end cap being linearly aligned to compress together in response to rotation of the adjusting mechanism in one direction in the larger receiver, which causes expansion of the adjusting mechanism and imposes a tension force on the specimen and thereby causes stress-strain in the specimen that is measured by the strain gage.

22. The apparatus of claim 21 further comprising at least one strain gage mounted on the exterior of at least one of the adjusting mechanism or the compression column for measuring stress-strain.

23. The apparatus of claim 21 further comprising an environmental chamber containing the first end, the test specimen, the adjusting mechanism, the compression column, the strain gage, and the second end cap and exposing the first end, the test specimen, the adjusting mechanism, the compression column, the strain gage, and the second end cap to high pressure hydrogen and wherein holes are formed in at least one of the end caps, the adjusting mechanism and the compression column to allow exposure of the specimen to the hydrogen environment of the chamber.

24. The apparatus of claim 21 further comprising flats formed on the exterior of the first end cap, the adjusting mechanism, and the compression column to facilitate rotation of the adjusting mechanism without rotating the first end cap relative to the second end cap.

* * * * *